US008070720B2

(12) United States Patent  (10) Patent No.: US 8,070,720 B2
Johnson  (45) Date of Patent: Dec. 6, 2011

(54) METHODS FOR INCORPORATING A DRUG INTO AN ELASTOMERIC MEDICAL DEVICE

(75) Inventor: David Johnson, Turloughmore (IE)

(73) Assignee: Medtronic Vascular, Inc, Santa Rosa, CA (US)

( * ) Notice: Subject to any disclaimer, the term of this patent is extended or adjusted under 35 U.S.C. 154(b) by 550 days.

(21) Appl. No.: 11/972,790

(22) Filed: Jan. 11, 2008

(65) Prior Publication Data

US 2009/0182273 A1  Jul. 16, 2009

(51) Int. Cl.
*A61M 29/00* (2006.01)
(52) U.S. Cl. ............... 604/103.02; 604/96.01; 623/1.42; 623/1.46
(58) Field of Classification Search ............... 604/96.01, 604/103.01, 103.02, 103.06, 103.08, 264, 604/265; 623/1.39, 1.4, 1.44–1.46; 427/198, 427/2.14; 106/672, 122; 216/56; 264/635; 521/50
See application file for complete search history.

(56) References Cited

U.S. PATENT DOCUMENTS

| 4,199,864 | A | * | 4/1980 | Ashman ................. 433/175 |
| 5,707,385 | A | | 1/1998 | Williams |
| 6,280,411 | B1 | | 8/2001 | Lennox |
| 6,544,221 | B1 | | 4/2003 | Kokish et al. |
| 6,656,156 | B2 | | 12/2003 | Yang et al. |
| 6,752,826 | B2 | * | 6/2004 | Holloway et al. ............ 623/1.13 |
| 6,989,071 | B2 | | 1/2006 | Kocur et al. |
| 7,011,654 | B2 | | 3/2006 | Dubrul et al. |
| 2001/0027307 | A1 | | 10/2001 | Dubrul et al. |
| 2002/0042645 | A1 | | 4/2002 | Shannon |
| 2002/0055710 | A1 | * | 5/2002 | Tuch ....................... 604/103.02 |
| 2003/0114791 | A1 | | 6/2003 | Rosenthal et al. |
| 2004/0267354 | A1 | * | 12/2004 | Ringeisen et al. ........... 623/1.42 |
| 2005/0181004 | A1 | | 8/2005 | Hunter et al. |
| 2007/0060863 | A1 | | 3/2007 | Goeken et al. |
| 2007/0225564 | A1 | | 9/2007 | Couvillon et al. |
| 2008/0140002 | A1 | * | 6/2008 | Ramzipoor et al. ..... 604/103.02 |
| 2009/0012603 | A1 | * | 1/2009 | Xu et al. ...................... 623/1.42 |

FOREIGN PATENT DOCUMENTS

EP  1 604 704  12/2005
* cited by examiner

*Primary Examiner* — Laura Bouchelle

(57) ABSTRACT

A method of manufacturing a drug delivery device includes forming a undercoat on an outer surface of a dipping mandrel, forming a tack coat on an outer surface of the undercoat, depositing granular particles on at least a portion of the tack coat, forming an overcoat on the formed tack coat, trapping the granular particles between the tack coat and the overcoat and removing an outermost portion of the overcoat to expose a portion of the granular particles. A system for treating a vascular condition includes a catheter having an inflation lumen, an elastomeric drug delivery device disposed on the catheter and in fluid communication with the inflation lumen, a plurality of expandable pores disposed within an outer layer of the elastomeric drug delivery device and at least one therapeutic agent disposed within at least a portion of the plurality of expandable pores.

4 Claims, 7 Drawing Sheets

FIG. 4
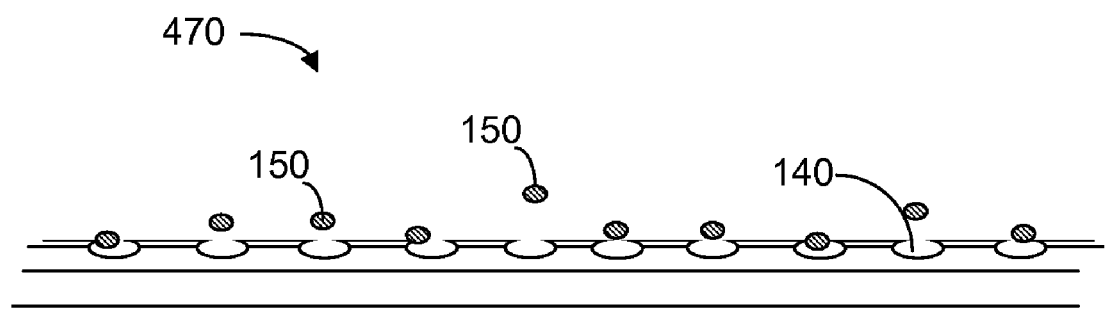
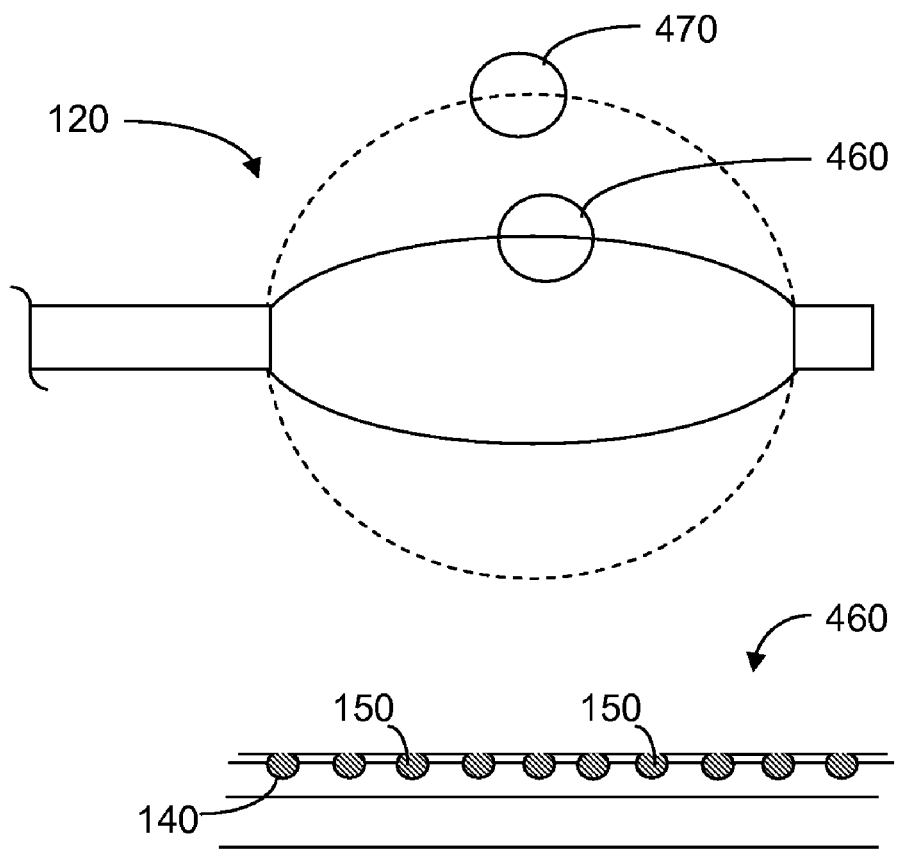

METHODS FOR INCORPORATING A DRUG INTO AN ELASTOMERIC MEDICAL DEVICE

TECHNICAL FIELD

This invention relates generally to treatment of vascular conditions. More specifically, the invention relates to methods for manufacturing a drug infused elastomeric device for delivering a drug into tissue adjacent a vascular plaque.

BACKGROUND OF THE INVENTION

Heart disease, specifically coronary artery disease, is a major cause of death, disability, and healthcare expense in the United States and other industrialized countries. A number of methods and devices for treating coronary artery disease have been developed, some of which are specifically designed to treat the complications resulting from atherosclerosis and other forms of coronary arterial narrowing.

One method for treating such vascular conditions is percutaneous transluminal coronary angioplasty (PTCA). During PTCA, a balloon catheter device is inflated to dilate a stenotic blood vessel. The stenosis may be the result of a lesion such as a plaque or thrombus. When inflated, the pressurized balloon exerts a compressive force on the lesion, thereby increasing the inner diameter of the affected vessel. The increased interior vessel diameter facilitates improved blood flow.

However, soon after the procedure, a significant proportion of treated vessels restenose. Various methods have been developed to prevent or inhibit this restenosis. One method is to provide a physical support in the form of a stent to maintain the increased interior diameter of the vessel lumen.

Stents are generally cylindrical shaped devices that are radially expandable to hold open a segment of a vessel or other anatomical lumen after implantation into the body lumen. Various types of stents are in use, including expandable and self-expanding stents. Expandable stents generally are conveyed to the area to be treated on balloon catheters or other expandable devices. For insertion, the stent is positioned in a compressed configuration along the delivery device. The stent may be crimped onto a balloon that is folded or otherwise wrapped about a guide wire that is part of the delivery device. After the stent is positioned across the lesion, it is expanded by the delivery device. For a self-expanding stents, a sheath is retracted that allows expansion of the stent.

Stents have been used with coatings to deliver drugs or other therapeutic agents at the site of the stent to assist in preventing inflammation, infection, thrombosis, and proliferation of cell growth that can occlude the vessel lumen. However, the coated stent can deliver drugs to only those portions of the vessel in contact with the stent. Because restenosis is often a greater problem in tissue adjacent to the ends of a stent than it is elsewhere along the stent, drug delivery using the stent alone may not be fully effective.

One drawback of current drug eluting stent technology is that the drug is combined with a polymer. In such drug coated stents the drug and polymer need to be combined in a common solution or suspension, thereby making it necessary to use a common solvent. In addition, when the drug is fully eluted the stent is left with non-functional polymer on the stent surface, which may be less biocompatible than the stent material itself.

Vascular delivery of drugs and other agents intended to inhibit restenosis has also been accomplished using devices that inject or otherwise infuse the agents into the treated portion of the vessel before, during, or after performing PTCA. Unlike coated stents, these devices deliver the antirestenosis agents without providing physical support for the treated vessel. One drawback to these devices is that the drug is delivered in discrete targeted locations within the tissue wall which may limit the effectiveness of the drug for limiting restenosis.

Thus, coated stents support the lumen of a vessel in an open position following PTCA but may be limited in their ability to deliver an anti-restenosis agent to the wall of the treated vessel. Therefore, it would be desirable to have a system and method for treating a vascular condition that overcome the aforementioned and other disadvantages.

SUMMARY OF THE INVENTION

One aspect of the present invention is a method of manufacturing an elastomeric drug delivery device. The method includes the limitations of forming a undercoat on an outer surface of a dipping mandrel; forming a tack coat on an outer surface of the undercoat; depositing a plurality of granular particles on at least a portion of the formed tack coat; forming an overcoat on an outer surface of the formed tack coat, wherein the deposited plurality of granular particles are trapped between the tack coat and the overcoat; and removing an outermost portion of the overcoat to expose a portion of the deposited granular particles.

Another aspect of the present invention is a system for treating a vascular condition including a catheter having an inflation lumen, an elastomeric drug delivery device disposed on the catheter and in fluid communication with the inflation lumen, a plurality of expandable pores disposed within an outer layer of the elastomeric drug delivery device and at least one therapeutic agent disposed within at least a portion of the plurality of expandable pores.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 4 is an illustration of one embodiment of an elastomeric drug delivery device, in accordance with the present invention;

DETAILED DESCRIPTION OF THE PRESENTLY PREFERRED EMBODIMENTS

Figure 1:
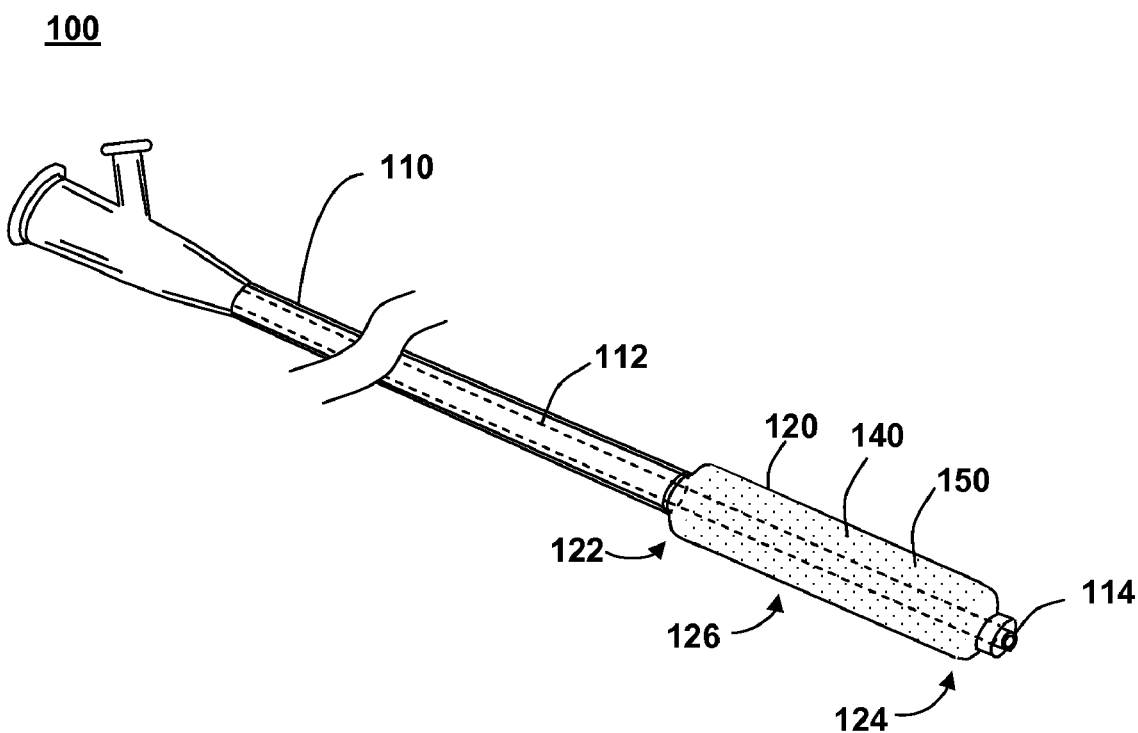
FIG. 1 is an illustration of one embodiment of a system for treating a vascular condition, in accordance with the present invention.

One aspect of the present invention is a system for treating a vascular condition. One embodiment of the system, in accordance with the present invention, is illustrated in FIG. 1. The system comprises catheter 110 and elastomeric drug delivery device 120. In one embodiment, elastomeric drug delivery device 120 is a balloon. Catheter 110 has an inflation lumen 112. In one embodiment, catheter 110 includes a therapeutic agent delivery lumen 114. Drug delivery balloon 120 comprises a proximal end portion 122, a distal end portion 124, and a center portion 126.

Catheter 110 may be any catheter known in the art for delivering a drug delivery balloon to a treatment site within a vessel. In one embodiment, catheter 110 is a percutaneous transluminal coronary angioplasty (PTCA) balloon catheter. Catheter 110 includes inflation lumen 112 for inflating balloon 120.

Drug delivery balloon 120 is formed from any biocompatible polymeric material having elastomeric characteristics. The elastomeric material may be, for example, silicone, polyurethane, cis-1,4 polyisoprene, polyvinyl, latex rubber, nitrile rubber, butyl rubber, SIBS elastomer, SIS elastomer, and combinations thereof. In one embodiment, balloon 120 is composed of a silicone elastomer. In another embodiment, balloon 120 is composed of urethane-silicone copolymer.

Drug delivery balloon 120 includes a plurality of expandable pores 140 disposed within at least a portion of an outer surface of the drug delivery balloon. Methods for the formation of the expandable pores 140 are discussed in more detail below.

A therapeutic agent 150 is disposed within the expandable pores 140. The therapeutic agent may include, for example, an antineoplastic agent, an antiproliferative agent, an antibiotic, an antithrombogenic agent, an anticoagulant, an antiplatelet agent, an anti-inflammatory agent, combinations of the above, and the like. Therapeutic agent 150 is disposed within expandable pores 140 by, for example, dipping, spraying. In another embodiment, a granular therapeutic agent 150 is disposed within expandable pores 140 in a fluidized bath, discussed in detail below.

Various other therapeutic agents include fibrinolytics, therapeutic proteins or peptides, recombinant DNA products, or other bioactive agents, diagnostic agents, radioactive isotopes, or radiopaque substances may be used depending on the anticipated needs of the targeted patient population. The formulation containing therapeutic agent 150 may additionally contain excipients including solvents or other solubilizers, stabilizers, suspending agents, antioxidants, and preservatives, as needed to deliver an effective dose of the therapeutic agent to the treatment site.

In one embodiment, therapeutic agent 150 is an anti-inflammatory agent such as, for example, paclitaxel, dexamethasone, hydrocortisone, salicylic acid, fluocinolone acetonide, corticosteroids and other drugs and prodrugs. In other embodiments, therapeutic agent 150 is an antiproliferative such as, for example, zotarolimus, sirolimus, everolimus, pimecorlimus, and other drugs having antiproliferative activity.

Figure 2:
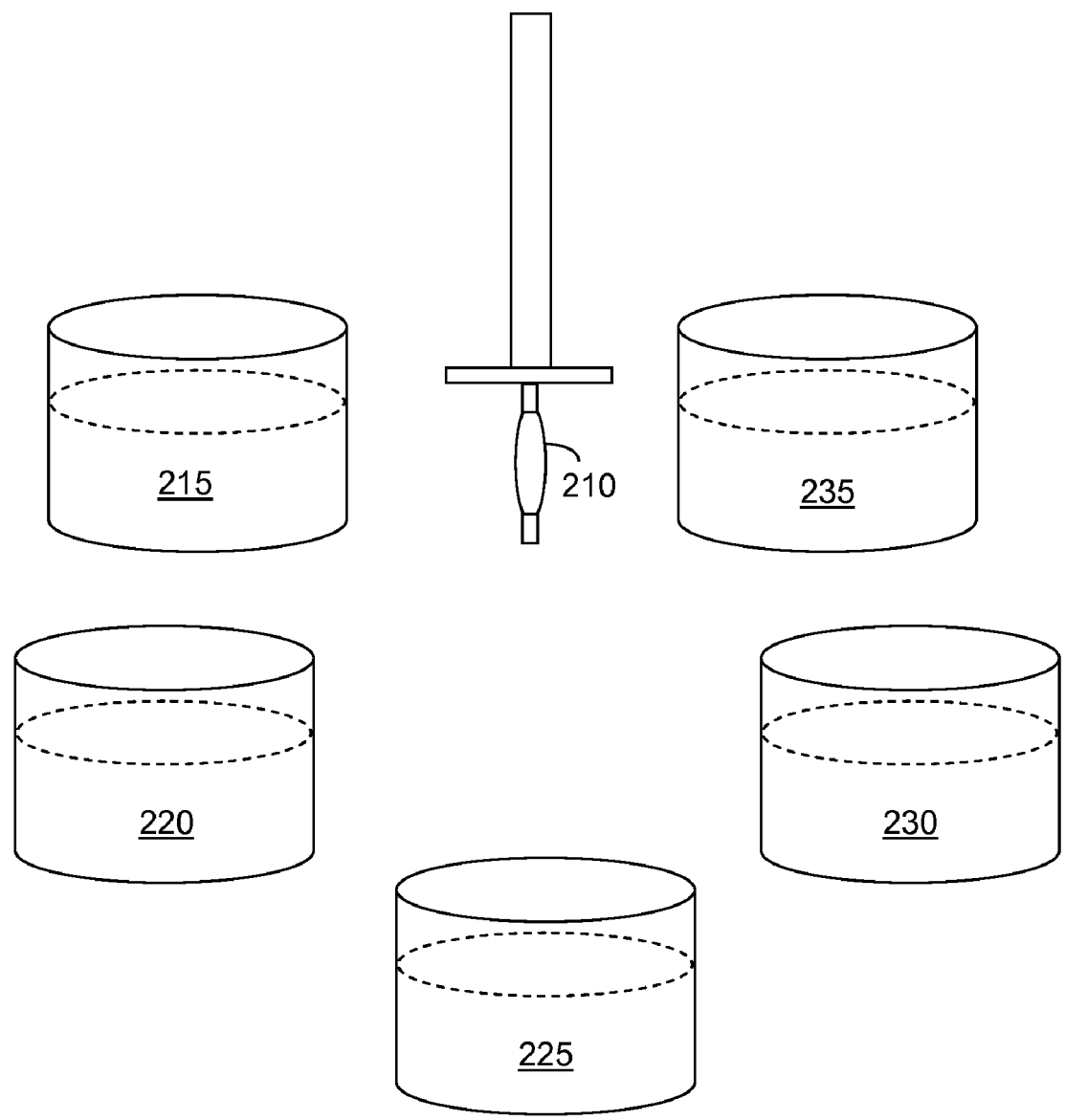
FIG. 2 shows one embodiment of a system for manufacturing an elastomeric drug delivery device, in accordance with the present invention.
Figure 3:
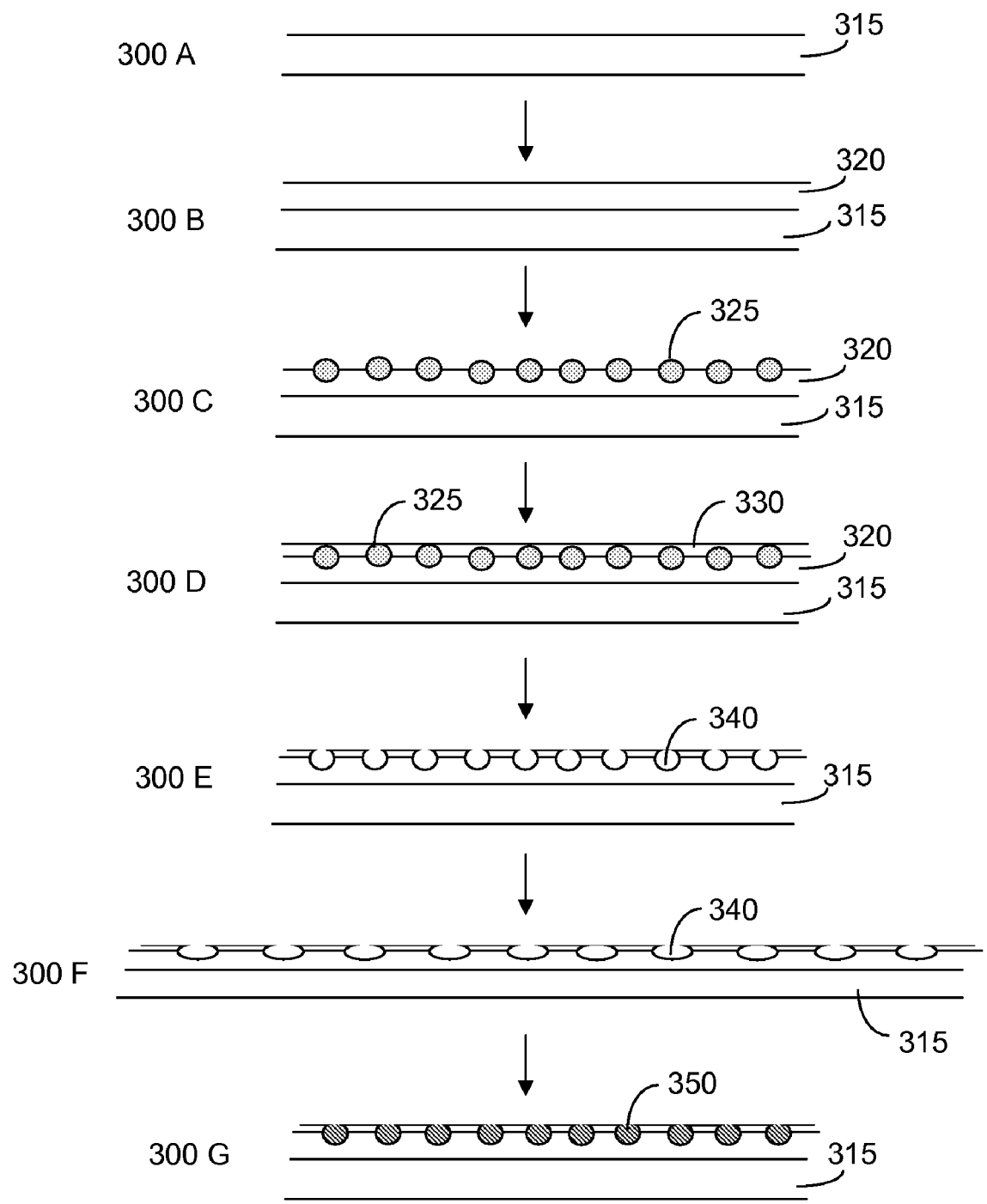
FIG. 3 schematically illustrates the manufacturing steps for one embodiment of an elastomeric drug delivery device, in accordance with the present invention.

With reference to FIGS. 2 and 3, the manufacture of one embodiment of an elastomeric drug delivery device 120 will be described. FIG. 2 illustrates one embodiment of a system 200 for manufacturing an elastomeric drug delivery device 120. FIG. 3 schematically illustrates, in step 300 A to step 300 G, one embodiment of a method 300 for manufacturing an elastomeric drug delivery device 120. Elastomeric drug delivery device 120 is formed on mandrel 210 using a dipping process. Mandrel 210 is a mold having on outer surface having dimensions and shape of the elastomeric drug delivery device 120. Elastomeric drug delivery device 120 comprises a plurality of layers, namely, an undercoat, 315, a tack coat 320 disposed on undercoat 315 and an overcoat 330 disposed on tack coat 320.

Undercoat 315 is formed on mandrel 210 by dipping the mandrel into a liquid undercoat medium 215 that contains the elastomeric polymer (Step 300 A). The liquid undercoat medium 215 may be latex or a solution of the polymer in an organic solvent. Organic solvents may be, for example, ethers, amines, esters or alcohols. In one embodiment, the liquid undercoat medium 215 is a solution of silicone and xylene. In another embodiment, under coat medium 215 is a solution of silicone and hexane. Dipping mandrel 210 into the liquid undercoat medium 215 and then withdrawing the mandrel will leave a film of the liquid medium over the outer surface of the mandrel. The thickness of undercoat 315 may be increased by dipping the mandrel multiple times in order to produce an undercoat of a desired thickness. The elastomeric film is partially cured on the mandrel between each dipping to allow for the adhesion of the next layer of polymeric material. The dipped mandrel may be air dried or cured at an elevated temperature. The length of time that the dipped mandrel is air dried or cured between dips to provide sufficient adhesion depends on such factors as type of polymer, type of solvent and the desired degree of viscosity. In one embodiment, the mandrel is air dried or cured for 1 second to 60 seconds at an elevated temperature between dips. In another embodiment, the dipped mandrel is air dried or cured for 1 minute to 3 minutes. In one embodiment, the dipped mandrel is air dried or cured at a temperature of between 60° F. and 100° F.

Tack coat 320 is deposited on an outer surface of undercoat 315 by dipping the mandrel with the undercoat into a tack coat solution 220 (Step 300 B). Tack coat solution 220 is a liquid polymeric medium having a higher viscosity than the liquid undercoat medium. The viscosity of the tack coat solution is controlled by the amount of solvent in the solution. A decreased amount of solvent provides a higher viscosity solution. Tack coat 320 may be composed of the same or similar elastomeric polymer as undercoat 315. The tack coat may be applied to the entire undercoat or any portion thereof. In one embodiment, a portion of the undercoat is masked before dipping the mandrel into the tack coat solution. The undercoated mandrel may be masked to suit a particular application. In one embodiment, the tack coat is partially air dried or cured to increase the tackiness of the layer prior to continuing with the next step.

Mandrel 210 having tack coat 320 is then immersed in a fluidized particle bath 225 (Step 300 C). Fluidized particle bath 225 is an aerated bath where air or other gas is passed through granular particles 325 to keep the particles mobile. In one embodiment, the fluidized particle bath is a fluidized salt bath. In one embodiment fluidized particle bath contains crystalline sodium chloride. Though granular salt is preferred, fluidized particle bath 225 may contain any particle that is soluble, as discussed in more detail below. The size and shape of expandable pores 140 are determined by the size and shape of the granular particle contained in the fluidized salt bath. In one embodiment, the expandable pores 140 are crystalline shaped pores corresponding to the size and shape of the crystalline structure of the fluidized particles.

When the tack coated mandrel is dipped into the fluidized salt, salt particles 325 adhere to the surface. The amount of granular salt that adheres to the tack coat depends on such factors as, for example, dipping technique, time of immersion, tackiness of the tack coat, air flow through the salt, and size of granular particles. The fluidized granular salt particles will adhere to those portions having a tack coat. The particles may be disposed on the tack coat by other methods, such as, for example, by spraying the particles. The mask, if present, may be removed after application of the tack coat or after application of the granular particles. In one embodiment, loose or poorly adhered particles may be removed after the mandrel is pulled from the fluidized particle bath.

Next (Step 300 D), mandrel 210 with adhered particles 325 is dipped into overcoat polymeric solution 230 to form overcoat 330. Overcoat polymeric solution may be the same solution as undercoat solution 215. In other embodiments, overcoat solution 230 includes a polymer different from the undercoat solution 215. Application of overcoat 330 is similar to or the same as the application of undercoat 215. Application of overcoat 330 traps particles 325 between the tack coat 320 and the overcoat 330. The thickness of overcoat 330 may be increased by performing additional dipping and drying cycles. Mandrel 210 is dipped and partially cured until the desired thickness of the overcoat is achieved. In one embodiment, the overcoat is applied in a series of dips so that the adhered salt particles are substantially covered by the overcoat polymer. Once the desired thickness is achieved, the overcoat may be fully cured before proceeding to the next step. In one embodiment, a final cure comprises a platinum cure carried out at 170° F. for 45 minutes followed by 135 minutes at 300° F. Those with ordinary skill in the art will appreciate that the final cure may be carried out at different combinations of time and temperature for the same affect. For example, the final cure may be carried out at lower temperatures for a longer period of time.

To form the plurality of expandable pores 140, the overcoat is scrubbed or otherwise brushed to remove a thin layer of the overcoat in order to break the surface and to expose the embedded soluble particles. Once exposed, the mandrel is placed in bath 235 to solubilize particles 335, leaving expandable pores 140 within the outer surface 330 of elastomeric drug delivery device 120, (Step 300 E). Elastomeric drug delivery device 120 is then removed from mandrel 210.

Once removed from mandrel 210, the expandable pores 140 of the formed elastomeric drug delivery device 120 may be loaded with one or more therapeutic agents 150. To load the pores, elastomeric drug delivery device 120 is inflated to open and expand pores 140 (Step 300 F). Once expanded, the therapeutic agent is applied. The therapeutic agent may be applied by any method known in the art such as, for example, by dipping, spraying, painting, wiping, rolling, printing and combinations thereof. In one embodiment, elastomeric drug delivery device 120 is secured to delivery catheter 110 prior to loading the therapeutic agent 150. In another embodiment, elastomeric drug delivery device 120 is secured to an inflation mandrel, loaded with therapeutic agent 150, removed from the inflation mandrel and secured to delivery catheter 110. Once the therapeutic agent 150 is applied, the elastomeric drug delivery device 120 is deflated thereby collapsing the pore openings to trap the therapeutic agent within the expandable pores 140 (Step 300 G).

FIG. 4 is a schematic illustration of elastomeric drug delivery device 120 in a deflated delivery state 460, showing the therapeutic agent 150 trapped within a plurality of expandable pores 140, and in an expanded therapeutic state 470 showing the expansion of pores 140 and the release of therapeutic agent 150 from the expanded pores.

Figure 5:
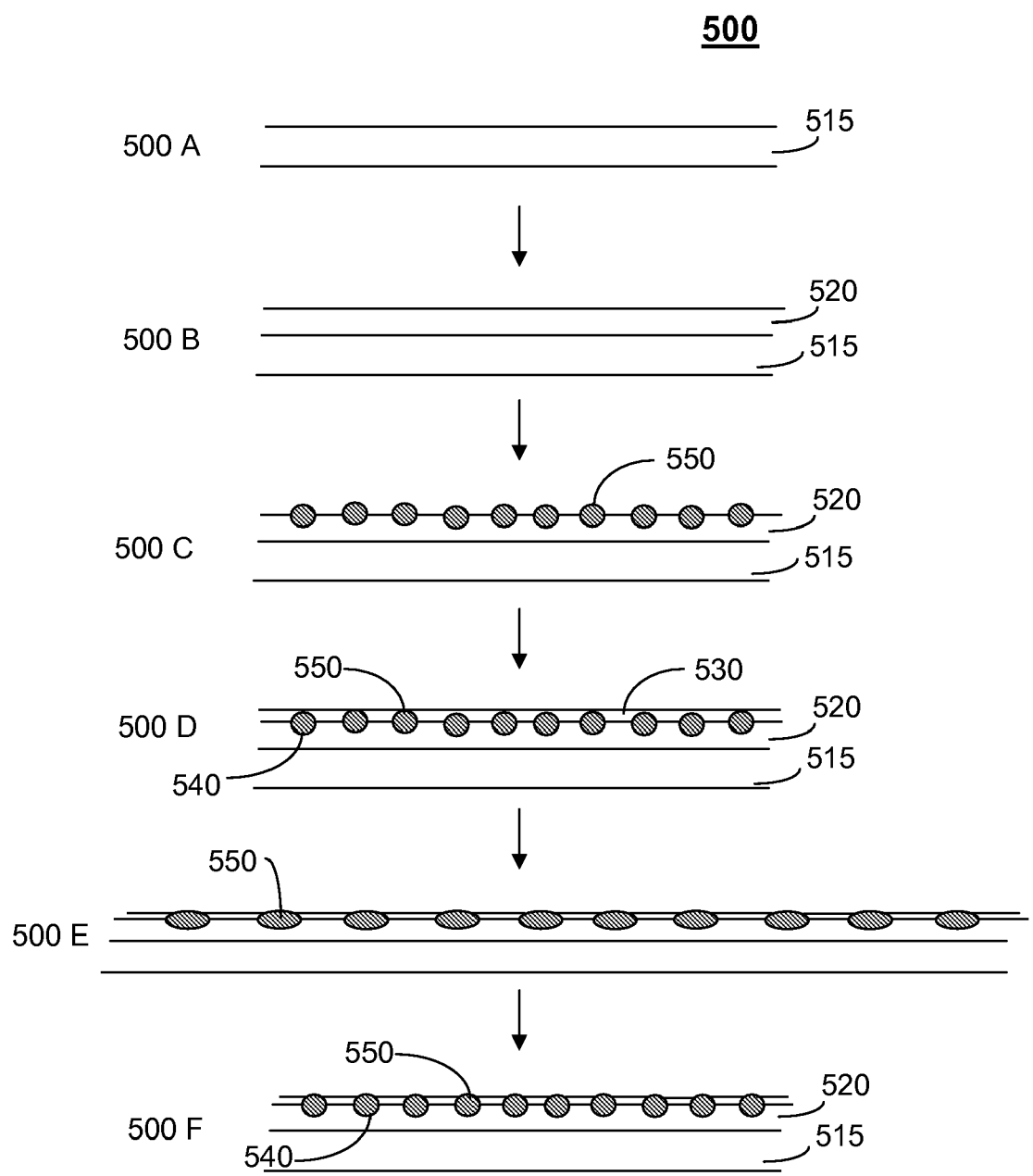
FIG. 5 schematically illustrates the manufacturing steps for another embodiment of an elastomeric drug delivery device, in accordance with the present invention.

FIG. 5 is a schematic illustration of steps 500 A to 500 F of another embodiment of a method 500 for manufacturing an elastomeric drug delivery device 520. The method of manufacture of elastomeric drug delivery device 520 is similar in many respects to the manufacture of elastomeric drug delivery device 120 described above and illustrated in FIGS. 2 and 3. Formation of elastomeric drug delivery device 520 begins with forming undercoat 515 on a mandrel (Step 500 A). Undercoat 515 is formed in the same or similar manner as described above for the formation of bases coat 315. Next, tack coat 520 is disposed on undercoat 515 (Step 500 B). Tack coat 520 is similar to or the same as tack coat 320 described above.

Next, mandrel 210 with the applied tack coat 520 is immersed in a fluidized bath of granular therapeutic agent 550 (Step 500 C). Therapeutic agent 550 may be any one or a combination of those listed above. The amount of therapeutic agent loaded onto the tack coat may depend on factors such as the size and shape of the granules. The amount of therapeutic agent may also be controlled by masking portions of the undercoat thereby limiting the tack coat and the amount of therapeutic agent that will adhere to the tack coated device.

Next, an overcoat 530 is applied to trap the therapeutic agent between the tack coat 520 and the overcoat 530 (Step 500 D). The trapped therapeutic agent 550 forms a plurality of expandable pores 540. Overcoat 530 is the same as or similar to overcoat 320 and is applied in the same manner, as discussed above. After application and drying of overcoat 530, elastomeric drug delivery device 520 is inflated and the overcoat is scrubbed or otherwise manipulated to break the surface and expose the trapped therapeutic agent (Step 500 E). Deflation of the elastomeric drug delivery device 520 retains the therapeutic agent within the drug delivery device (Step 500 F). The elastomeric drug delivery device 520 may be secured to a delivery catheter for inflation and scrubbing or may be retained on a separate device suitable for inflation and scrubbing. In this case, the scrubbed and deflated elastomeric drug delivery device 520 is then removed and secured to a delivery device.

Figure 6:
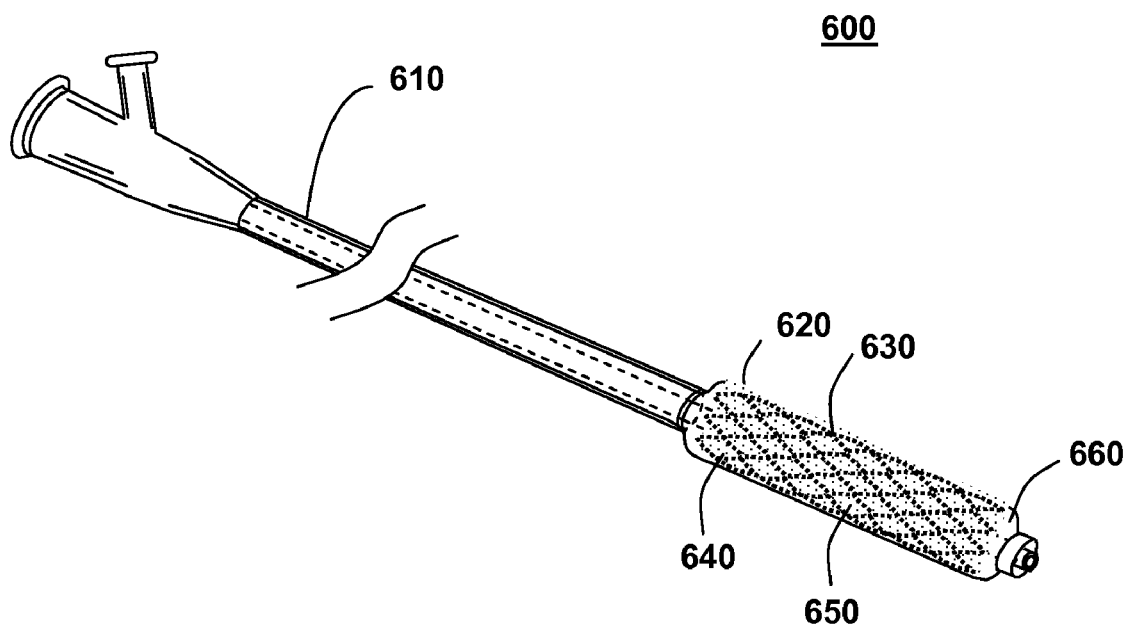
FIG. 6 is an illustration of another embodiment of a system for treating a vascular condition, in accordance with the present invention.

Another embodiment of the system, in accordance with the present invention, is illustrated in FIG. 6. System 600 comprises catheter 610 and elastomeric drug delivery device 620. Elastomeric drug delivery device 620 disposed on an outer surface of stent 630. In one embodiment, stent 630 is a balloon expandable stent disposed on balloon 660. Stent 630 is composed of a biocompatible metallic or polymeric material or combinations thereof. Stent 630 may be any stent suitable for a particular application.

In this embodiment, elastomeric drug delivery device 620 is an expandable sheath. Expandable sheath 620 is attached to stent 630 by, for example, sutures, adhesive, welding or combinations thereof. In one embodiment, expandable sheath 620 comprises a graft portion of a stent/graft assembly.

Expandable sheath 620 includes a plurality of expandable pores 640. Expandable pores 150 include at least one therapeutic agent disposed therein. In one embodiment, the manufacture and drug loading of elastomeric drug delivery device 620 is the same as or similar to the manufacture and drug loading of elastomeric drug delivery device 120. In another embodiment, the manufacture and drug loading of elastomeric drug delivery device 620 is the same as or similar to the manufacture and drug loading of elastomeric drug delivery device 520. In either embodiment, the shape of the mandrel for use in the dipping process is configured to form an essentially tubular shaped elastomeric device that, in additional steps, is formed into an open ended tube or sheet that is then attached to the outer surface of the stent. In one embodiment, the ends of the elastomeric device are removed to form an open ended cylinder. In another embodiment, the ends are removed and the resulting cylinder is split lengthwise to form a sheet that is wrapped around the stent.

In use, the expansion of the stent at the treatment site results in the expansion of elastomeric drug delivery device 620. Expanding the elastomeric drug delivery device 620 causes pores 640 to expand and release the enclosed therapeutic agent, as described above.

In another embodiment, stent 630 is a self expandable stent. In this embodiment, system 600 does not necessarily require a balloon to expand stent 630 when delivered to the treatment site.

Figure 7:
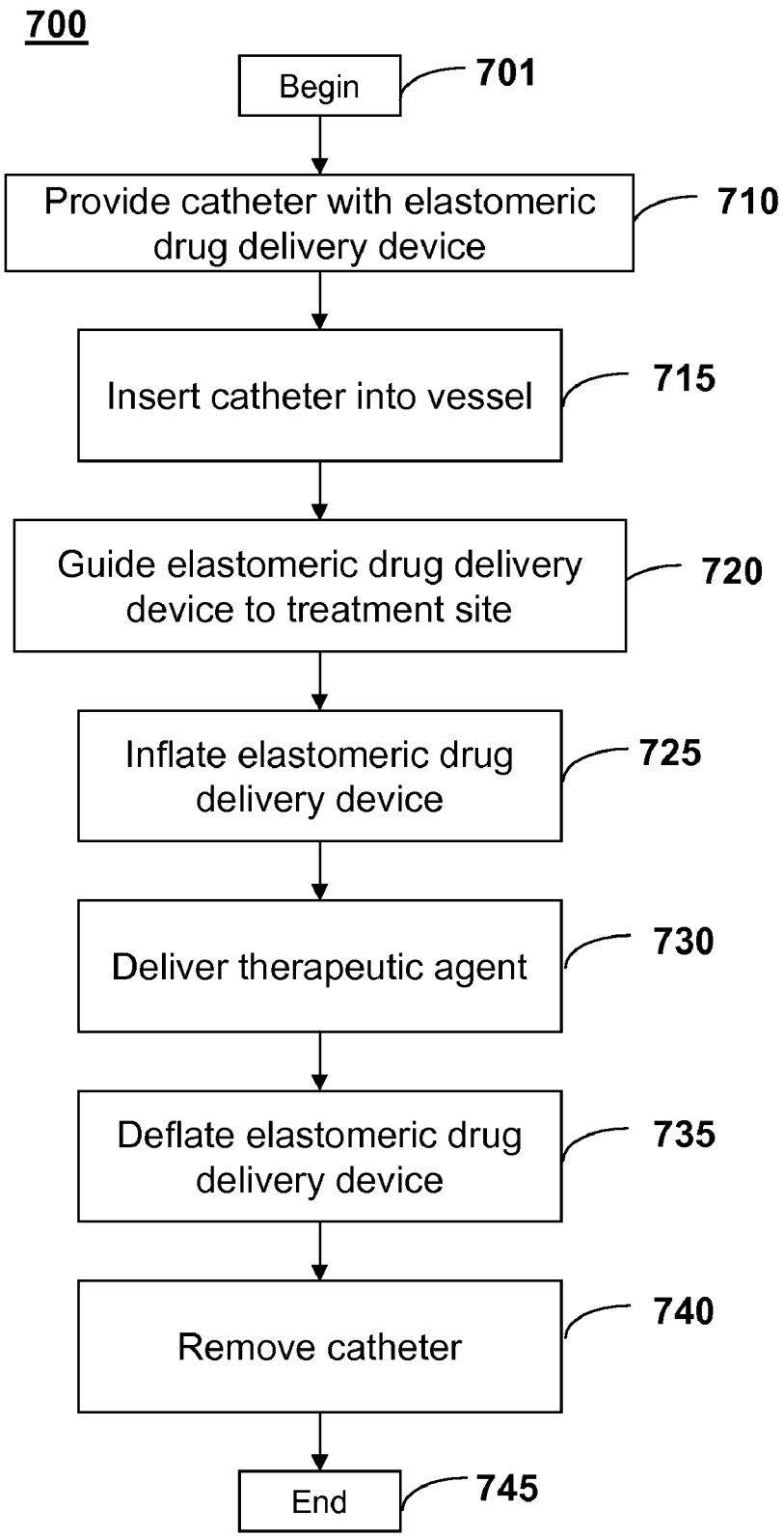
FIG. 7 is a flow diagram of one embodiment of a method of manufacturing an elastomeric drug delivery device for treating a vascular condition, in accordance with the present invention.

Another aspect of the present invention is a method of treating a vascular condition. FIG. 7 shows a flow diagram of one embodiment of the method 700 in accordance with the present invention. Method 700 begins at 701.

A system is provided comprising a delivery catheter 110 having an inflation lumen, and an elastomeric drug delivery device 120 disposed on the catheter (Block 710). The elastomeric drug delivery device 120 includes a plurality of expandable pores 140 disposed within an outer surface of device 120. At least one therapeutic agent 150 is loaded within at least a portion of the expandable pores.

The catheter and the elastomeric drug delivery device are introduced into a vessel containing a target region identified for treatment (Block 715) and guided to a position adjacent to the target region (Block 720). Once the elastomeric drug delivery device is in position, the elastomeric drug delivery device is inflated (Block 725).

Inflation of the elastomeric drug delivery device expands pores 140 to release one or more therapeutic agents 150. The one or more therapeutic agents 150 disposed within pores 140 are delivered into the wall of the target region of the vessel (Block 730).

Once one or more therapeutic agents have been delivered to the wall of the vessel, the elastomeric drug delivery device is deflated (Block 735) and the system and elastomeric drug delivery device are removed from the vessel (Block 740). Method 700 ends at 745.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of manufacturing an elastomeric drug delivery device, the method comprising:
    forming an undercoat on an outer surface of a dipping mandrel;
    forming a tack coat on an outer surface of the undercoat;
    depositing a plurality of granular particles on at least a portion of the formed tack coat;
    forming an overcoat on an outer surface of the formed tack coat, wherein the deposited plurality of granular particles are trapped between the tack coat and the overcoat; and
    removing an outermost portion of the overcoat to expose a portion of the deposited granular particles prior to insertion into a patient, wherein the plurality of granular particles comprises at least one therapeutic agent.

2. The method of claim 1 wherein the at least one therapeutic agent is chosen from a group consisting of an antineoplastic agent, an antiproliferative agent, an antibiotic, an antithrombogenic agent, an anticoagulant, an antiplatelet agent, and an anti-inflammatory agent.

3. The method of claim 1 wherein the therapeutic agent is an anti-inflammatory agent chosen from a group consisting of paclitaxel, dexamethasone, hydrocortisone, salicylic acid, fluocinolone acetonide, and corticosteroids.

4. The method of claim 1 wherein the therapeutic agent is an antiproliferative agent chosen from a group consisting of zotarolimus, sirolimus, everolimus, and pimecorlimus.

* * * * *